US010092899B2

(12) United States Patent
Heintzelman

(10) Patent No.: US 10,092,899 B2
(45) Date of Patent: Oct. 9, 2018

(54) PIPETTE TIP SYSTEM, DEVICE AND METHOD OF USE

(71) Applicant: Dale Lee Heintzelman, Bear, DE (US)

(72) Inventor: Dale Lee Heintzelman, Bear, DE (US)

(73) Assignee: Beacon Technologies, LLC, Bear, DE (US)

( * ) Notice: Subject to any disclaimer, the term of this patent is extended or adjusted under 35 U.S.C. 154(b) by 0 days.

(21) Appl. No.: 15/472,327

(22) Filed: Mar. 29, 2017

(65) Prior Publication Data

US 2017/0197207 A1 Jul. 13, 2017

Related U.S. Application Data

(62) Division of application No. 15/112,792, filed as application No. PCT/US2015/038517 on Jun. 30, 2015, now Pat. No. 9,638,608.

(60) Provisional application No. 62/019,378, filed on Jun. 30, 2014.

(51) Int. Cl.
| | |
|---|---|
| *G01N 1/10* | (2006.01) |
| *B01L 3/02* | (2006.01) |
| *B01L 9/00* | (2006.01) |
| *G01N 21/59* | (2006.01) |

(52) U.S. Cl.
CPC ............. *B01L 3/0275* (2013.01); *B01L 9/543* (2013.01); *G01N 21/59* (2013.01); *B01L 2200/025* (2013.01); *B01L 2200/026* (2013.01); *B01L 2300/0654* (2013.01); *B01L 2300/168* (2013.01)

(58) Field of Classification Search
CPC .... G01N 21/05; G01N 21/03; G01N 21/0303; G01N 30/74; G01N 21/031
USPC .......................................................... 356/246
See application file for complete search history.

(56) References Cited

U.S. PATENT DOCUMENTS

| | | | | |
|---|---|---|---|---|
| 2004/0033610 | A1* | 2/2004 | Lovell ................... | B01L 3/5085 436/43 |
| 2011/0317146 | A1* | 12/2011 | Gu ........................... | G01C 3/10 356/4.03 |
| 2012/0224179 | A1* | 9/2012 | Page ....................... | B01L 3/021 356/440 |
| 2012/0270310 | A1* | 10/2012 | Spence ................... | B01L 3/021 435/305.1 |

* cited by examiner

*Primary Examiner* — Md M Rahman
(74) *Attorney, Agent, or Firm* — Veritay Group IP; Susan B Fentress

(57) ABSTRACT

This disclosure is directed to exemplary embodiments of systems, methods, techniques, processes, products and product components that can facilitate users making improved absorbance or fluorescence measurements in the field of spectroscopy with reduced (minimal) sample waste, and increased throughput, particularly in the study of biological sciences. A measuring system is provided having: a base unit with a means for locating a pipette tip; a pipette tip designed to interact with the base unit for purposes of accurate pipette tip positioning; at least one light supplying unit positioned to supply light to a liquid sample in the pipette tip and at least one light collecting unit positioned to collect light from a liquid sample in the pipette tip.

14 Claims, 7 Drawing Sheets

PIPETTE TIP SYSTEM, DEVICE AND METHOD OF USE

CROSS REFERENCE TO RELATED APPLICATIONS

This application is a divisional application of U.S. patent application Ser. No. 15/112,792 filed Jul. 20, 2016, which is a § 371 National Stage Application of PCT/US15/038517 application filed 30 Jun. 2015 and U.S. provisional patent application Ser. No. 62/019,378 filed 30 Jun. 2014, under 35 U.S.C. § 111(a) (hereby specifically incorporated herein by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DISC APPENDIX

None.

FIELD OF THE INVENTION

This disclosure is directed to exemplary embodiments of systems, methods, techniques, processes, products and product components that can facilitate users making improved absorbance or fluorescence measurements in the field of spectroscopy with reduced (minimal) sample waste, and increased throughput, particularly in the study of biological sciences, with an objective, among others, of providing a unique, efficient solution to accurate absorbance/fluorescence measurements of liquid samples, and a reduction in equipment maintenance requirements.

DESCRIPTION OF THE RELATED ART

Conventionally, there are two principal methods, techniques or processes by which liquid samples are measured and analyzed.

The first conventional method involves use of a cuvette. A cuvette is a small tube generally of circular or square cross section, sealed at one end, and formed of a plastic material, glass, or fused quartz (for implementations that can involve the use of ultra-violet (UV) light). Cuvettes are designed to hold samples for spectroscopic experiments and analyses. Cuvettes are formed to have particular cross-sectional lengths, often 10 mm across, to allow for easy calculations of levels of illumination and/or coefficients of absorption.

Cuvettes are filled with liquid samples and light from a particular light source is shone through the liquid samples, the light from the particular light source often being specifically regulated through a series of intervening optics structures on a light supplying or incident side of the cuvette and correspondingly on a light collecting or recovery side of the cuvette. The involved optical elements can include, for example, integrating spheres, an intention of which is to normalize the light passed through the liquid sample from the light supplying components and recovered by light collecting components. The collected light, having passed through the liquid sample, is then passed generally to a spectrometer to evaluate absorption of the light by the liquid sample, i.e., intensity of the collected light at various wavelengths.

Cuvettes are generally not considered to be disposable items and, therefore, must be thoroughly washed between sample measurements in order to avoid contaminating the sample measurements. Further, cuvettes, and the processing of liquid sample measurements using those cuvettes, tend to waste a significant amount of a particular liquid sample.

The second method involves the spectroscopic measuring of liquid samples via a process by which microliter volume liquid samples are held by surface tension between two structural (anvil) surfaces. The anvil surfaces are highly polished, and generally include embedded optical fibers with ends finished flush with the anvil surfaces. Generally, one of the anvils is fixed, and the other of the anvils is movable to precisely control a distance between the anvils over which the absorption of the light by the liquid sample can be measured. U.S. Pat. No. 7,397,036 to Robertson et al., issued Jul. 8, 2008, describes such an exemplary measurement apparatus and method. A liquid sample is deposited on a small pedestal. The deposited liquid sample is then engaged by the anvils and essentially stretched as a liquid column supported between the anvil surfaces by surface tension in the liquid sample.

This method, which still requires contact of elements of the measuring device with the liquid sample, also requires specific cleaning of the device surfaces between sample measurements in order to avoid contaminating subsequent liquid samples leading to potentially erroneous measurements. This cleaning must be carefully undertaken in order to not affect the cleaned and polished nature of the anvils and embedded optical elements in a manner that can adversely affect liquid sample adherence retention, and/or the optical analysis.

BRIEF SUMMARY OF THE INVENTION

As will be described in specific detail below, the disclosed embodiments are directed to a unique pipette tip product that can address certain of the shortfalls in the conventional systems described above according to one or more of the following functional objectives.

Exemplary embodiments of the systems and methods according to this disclosure can provide a unique pipette tip product for implementing the quantifying of concentrations of solid components in solution in liquid samples. In embodiments, the solid components can include biological specimens such as, for example, proteins and nucleic acids, in the liquid samples.

Exemplary embodiments can provide for a pipette tip being inserted into a measurement system, the measuring system preferably having features for locating, and positioning the pipette tip appropriately to support the analysis of the liquid sample.

In embodiments, the pipette tip can have, or be arranged to have, a particular cross-sectional length in a light traversing direction in order to facilitate a spectroscopic analysis of the liquid sample in the pipette tip across the particular cross-sectional length.

In embodiments, the pipette tip can be held by any part of the tip or pipette in the measurement system structure, appropriately positioned between the measurement mechanics of the structure.

In embodiments, the pipette tip can be ejected from, or remain connected to, the pipette when the pipette tip is properly positioned between the measurement mechanics of the measurement system structure.

In embodiments, the pipette tip can be an integrated part of a transfer, bulb, or other single piece liquid collecting apparatus.

Exemplary embodiments can provide a specifically-cooperating light source with particular optics included for generating and projecting light onto an incident side of the pipette tip, and through the liquid sample, for collection on a recovery side of the pipette tip by light collecting elements. In embodiments, the light source can comprise one or more of a deuterium flash, a xenon flash lamp, a light emitting diode (LED), or other appropriate like light source. The light source can generally supply generated light to one or more of a fiber optics cable, a light pipe, or other light carrying/conveying medium. Combinations of these features can be generally referred to throughout this disclosure as a "light supplying unit".

Exemplary embodiments can provide that the light emitted by the light supplying unit can be made to pass through the disclosed pipette tip containing the liquid sample, and to be collected by a "light collecting unit." The light collecting unit can be comprised of one or more of a second fiber optics cable, light pipe, or other light carrying/conveying medium.

In embodiments, one or both of the light supplying unit and the light collecting unit can further comprise certain optics adjustment components, including, but not limited to, one or more lenses, mirrors, windows, and/or filters between the light supplying unit and the pipette tip and/or between the pipette tip and the light collecting unit.

In embodiments, the light supplying unit and the light collecting unit can be comprised of multiple cooperating output ports and input ports, respectively. These multiple numbers of cooperating output ports and input ports can be generally arranged in a structure commonly referred to as a multiplexer.

In embodiments, the light supplying unit and the light collecting unit can be one or both movable by means of manual or automatic operation with respect to each other in order that the one or both of the light supplying unit and the light collecting unit can be movable closer to, or farther away from, the disclosed pipette tip, which can or cannot be used for positioning the pipette tip and/or optics.

In embodiments, the pipette tip and/or pipette can be movable by means of manual or automatic operation in order to align the measurement area with the light supplying/collecting units.

Exemplary embodiments can provide that the light collecting unit passes collected light, having traversed through the liquid sample in the pipette tip, to a spectrometer or similar detector for light intensity/absorption measurements. Resulting measurements can be related, via, for example, a processing device, to one or more reference values that can be usable to calculate a concentration of the liquid sample according to known means and techniques.

Exemplary embodiments can provide a capacity to recover the pipette tip with the liquid sample inside allowing for no cross contamination of liquid samples, realizing minimal (essentially no) sample loss due to measurement, and substantially obviating any requirement to clean sample measurement surfaces between sample measurements, i.e., significantly reducing time-consuming maintenance requirements between sample measurements.

This disclosure provides, in one embodiment, a device made of a base unit configured to receive a pipette tip, the base unit is configured to provide structural alignment of the pipette tip between a light supplying unit and a light collecting unit mounted to the base unit, wherein the base unit has an inner profile defining an accommodating space, and wherein the inner profile of the base unit is configured to physically interact with an outer profile of a component unit configured to secure a pipette tip.

This disclosure provides, in another embodiment, a measuring system made of: a base unit having an inner profile defining an accommodating space; a component unit configured to secure a pipette tip and the component unit having an outer profile configured to physically interact with the inner profile of the base unit; at least one light supplying unit positioned to supply light to a liquid sample in the pipette tip and at least one light collecting unit positioned to collect light from a liquid sample in the pipette tip. The component unit can be removable or integrated into the pipette tip as part of the manufacturing process.

This disclosure provides, in another embodiment, a method to insert a discrete pipette tip into a light measuring system including the steps of: providing a device made of a base unit configured to receive a pipette tip, the base unit being configured to provide structural alignment of the pipette tip between a light supplying unit and a light collecting unit mounted to the base unit, wherein the base unit has an inner profile defining an accommodating space and wherein the inner profile of the base unit is configured to physically interact with an outer profile of a component unit configured to secure a pipette tip and inserting a pipette tip into the device.

BRIEF DESCRIPTION OF SEVERAL VIEWS OF THE DRAWING(S)

The invention can be best understood by those having ordinary skill in the art by reference to the following detailed description when considered in conjunction with the accompanying drawings in which.

DETAILED DESCRIPTION OF THE INVENTION

Figure 1:
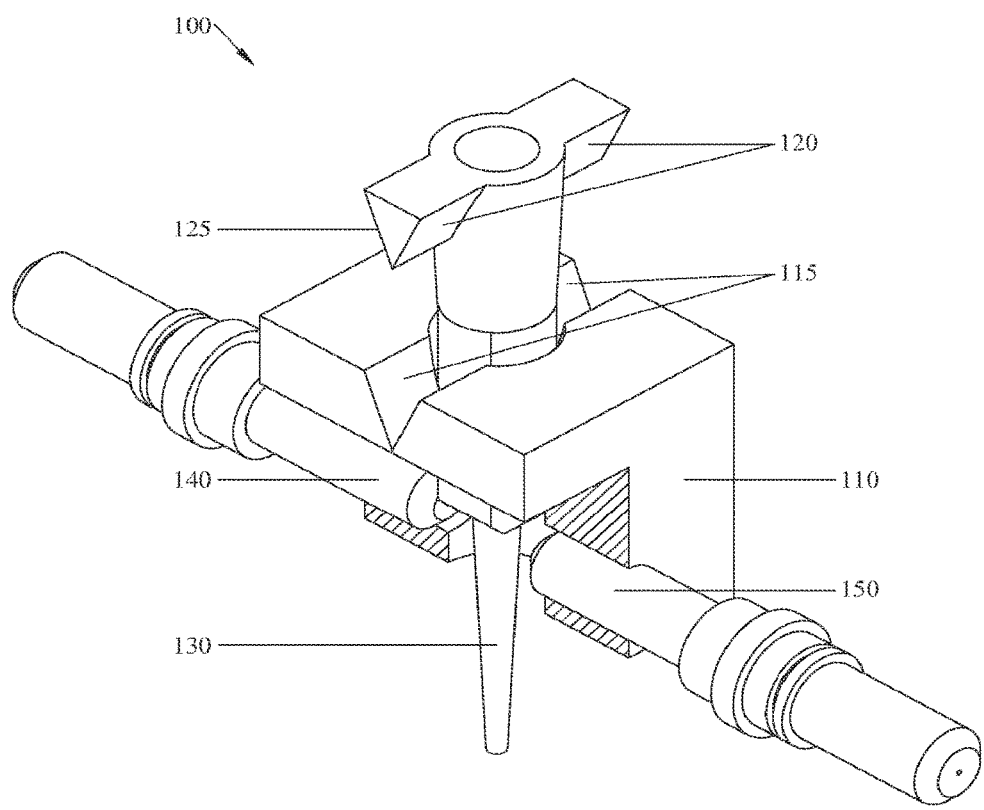
FIG. 1 illustrates a cross-sectional view of an exemplary embodiment of the measuring system structure.

Now referring to FIG. 1, an exemplary embodiment is provided of a measuring system 100 made of a base unit 110 within which a pipette tip 130 can be inserted with the objective of measuring light transmission in a repeatable manner. The base unit 110 provides a means to make the measurements through the use of at least one light supplying unit 140 positioned to supply light to a liquid sample in the pipette tip and at least one light collecting unit 150 positioned to collect light from a liquid sample in the pipette tip 130.

The exemplary measuring system structure 100 can include, for example, a base unit 110 and a component unit 120. The component unit 120 is configured to secure a pipette tip 130. To secure in this context means that the component unit 120 can be removable or an integrated part of the pipette tip 130.

The component unit 120, if removable, can be specifically configured to secure the pipette tip 130. The pipette tip 130 can be secured by any conventional means to the component unit 120, if removable. The pipette tip 130 can be secured to component unit 120, if removable, for example, by a snap fit, friction fit, or any other similar mechanical means of joining two parts together in a non-permanent manner. Alternatively, the component unit 120 can be permanently secured to the pipette tip 130 during the manufacturing process.

An outer profile 125 of the component unit 120 can be configured to physically interact with an inner profile 115 of an accommodating space in the base unit 110. This physical interaction between the outer profile 125 of the component unit 120 and the inner profile 115 of the base unit 110 can provide controlled structural alignment of the pipette tip 130 between a light supplying unit 140 and a light collecting unit 150 fixedly or movably mounted in the base unit 110.

An advantage of the illustrated and described physical interaction between the outer profile 125 of the component unit 120 and the inner profile 115 of the base unit is that it provides an essentially self-aligning structure for repeatable positioning of the pipette tip 130 that substantially obviates a requirement, such as can be required in the conventional microliter volume drop method discussed above, for the user to be exceptionally precise in guiding the pipette tip 130 to a particular pedestal on which the sample volume drop can be deposited.

Another advantage of the exemplary physical embodiments according to this disclosure is that they further remove a requirement for ejecting the liquid sample material from the pipette tip, thereby further obviating the attendant requirement to clean surfaces within, for example, the accommodating space in the base unit 110, or any of the associated structural components of the exemplary measuring system structure 100, as depicted. In other words, the liquid sample need never touch any of the surfaces of the structure but can, in all instances, remain substantially within the pipette tip 130.

Generally, the disclosed pipette tip 130 is a liquid collecting tip for a pipette that fits onto the pipette. In embodiments, the pipette tip 130 can be attached to, and/or removable from, the pipette. The attachment to the pipette tip 130 can be accomplished using standard methods including, for example, a snap or press fit to the pipette. More broadly, the pipette tip 130 can be held in place by means of physical pressure, magnetism, gravity, suction, or any similar method upon a surface of the pipette tip 130 or the pipette body itself. When removable/detachable from the pipette, the pipette tip 130 can be a disposable component. Otherwise, when removable/detachable from the pipette, the pipette tip 130 can be a cleanable and reusable component. The pipette tip 130 can be formed of any geometry in order to substantially prevent loss of the liquid sample if ejected from the pipette.

The pipette tip 130 can be formed of an optically clear material. The pipette tip 130 can have applied to it appropriate light transmittance zones or features in one or multiple areas in order for light to pass through with minimal interruption.

Figure 2:
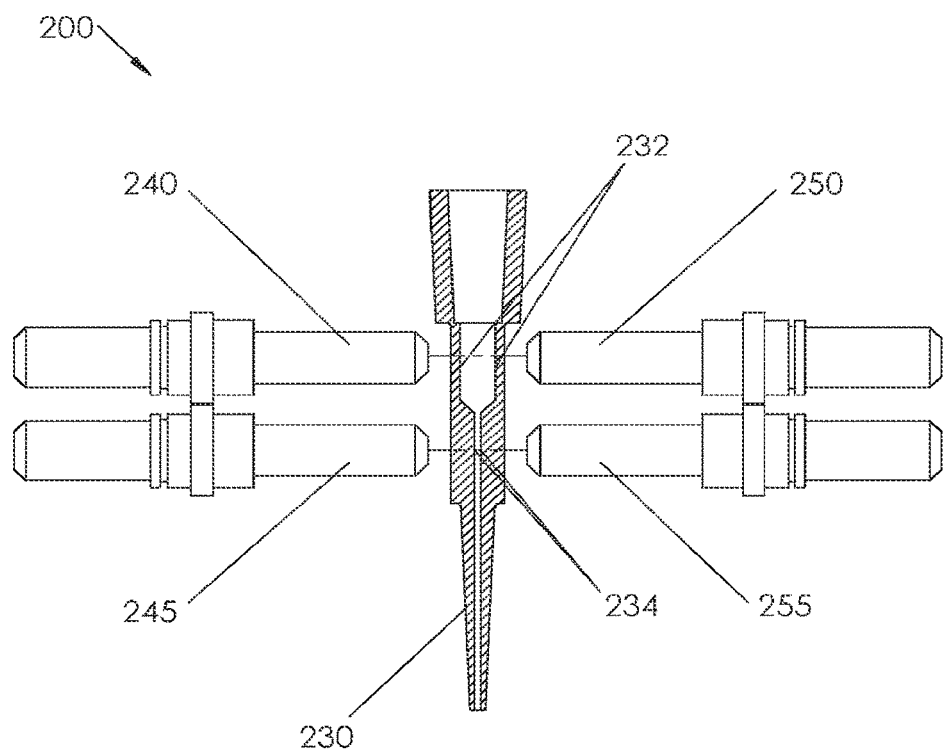
FIG. 2 illustrates an elevational view of exemplary embodiment of the system.

FIG. 2 illustrates a first exemplary embodiment 200 for an exemplary pipette tip 230 according to this disclosure. As shown in FIG. 2, the exemplary pipette tip 230 can be formed, or otherwise configured, to have at least one flat area (parallel flat(s)) 232,234. Optically clear areas of the exemplary pipette tip 230 can be parallel flats 232,234 with specified, yet different cross-sectional lengths. The parallel flats 232,234 can be formed of plastic, glass, ceramics, or any like flat clear material. There can be one or multiple areas with these parallel flats 232,234 formed in the pipette tip 230 at multiple distances apart. The parallel flats 232,234 can be alignable, based on the configuration of the measuring system structure, with a plurality of pairs of light supplying units/light collecting units 240/250, 245/255.

Now referring to FIG. 2, it should be noted that the plurality of pairs of light supplying units/light collecting units 240/250, 245/255 need not be aligned with each other along a same axis of penetration of the liquid sample. Rather, they can be aligned to penetrate the pipette tip 230 and liquid sample in a transverse direction at various angles.

The parallel flats 232,234 can transmit wavelengths of light that are intended for the liquid sample under observation, measurement and analysis. A preferred embodiment can comprise one or more parallel flats 232,234 that transmit an entire encompassing range of wavelengths, i.e. quartz. Ease of manufacture and compatibility of materials can be issues easily addressed in such an embodiment. Certain plastics, for example, can transmit a high wavelength range. Polypropylene, and certain polycarbonates, can, for example, be usable for forming the parallel flats 232,234. The parallel flats 232,234 can be formed according to conventional forming methods including, for example, blow molding, injection molding, deposit molding and the like.

The parallel flats 232,234 can be formed, and/or placed, to particularly define one or more known cross-sectional path lengths through the liquid sample.

Figure 3:
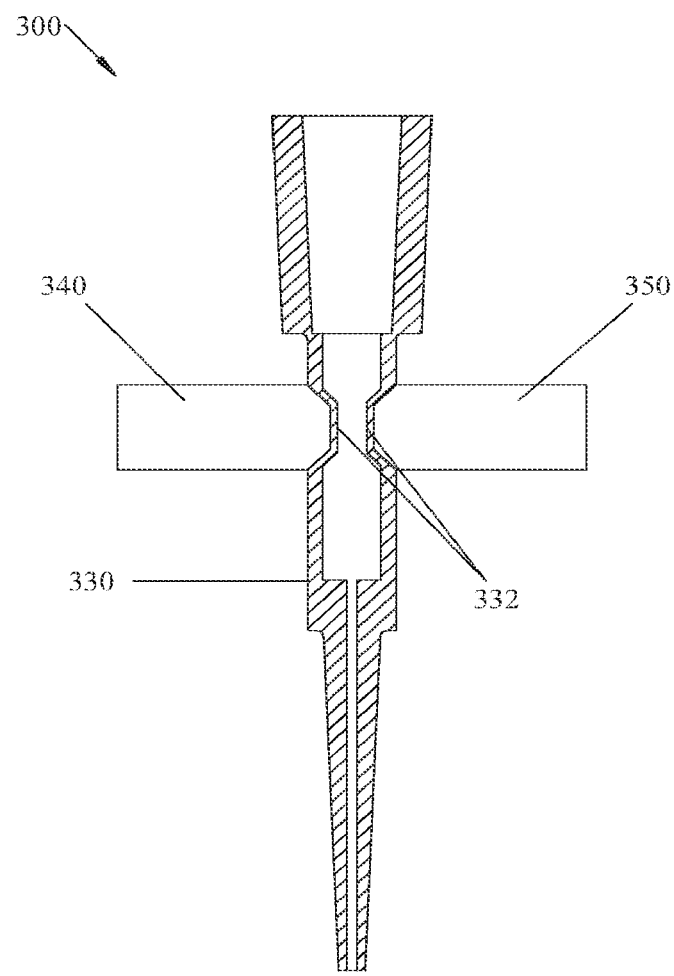
FIG. 3 illustrates an elevational view of exemplary embodiment of the system.

Now referring to FIG. 3, a second exemplary embodiment 300 for an exemplary pipette tip 330 according to this disclosure is provided. As shown in FIG. 3, the exemplary pipette tip 330 can be formed, or otherwise configured, to have at least one flexible area 332. Optically clear areas of the exemplary pipette tip 330 can be movable through interaction with the pair of light supplying unit/light collecting unit 340/350, to specify variable cross-sectional lengths for the liquid sample under observation, measurement and analysis. It should be noted that the position of one or both of the light supplying unit 340 and the light collecting unit 350 can be movable with respect to the position of the pipette tip 330 to squeeze the at least one flexible area 332 between the light supplying unit 340 and the light collecting unit 350 to change the path length.

The at least one flexible area 332 in the pipette tip 330 can be comprised of one or multiple flexible areas that are optically clear with application of appropriate light transmittance and can be constructed of any appropriate flexible material. The flexible areas can be squeezed (or pulled) to different distances between optics, including the light supplying unit 340 and the light collecting unit 350, or by other means, as appropriate.

Figure 4:
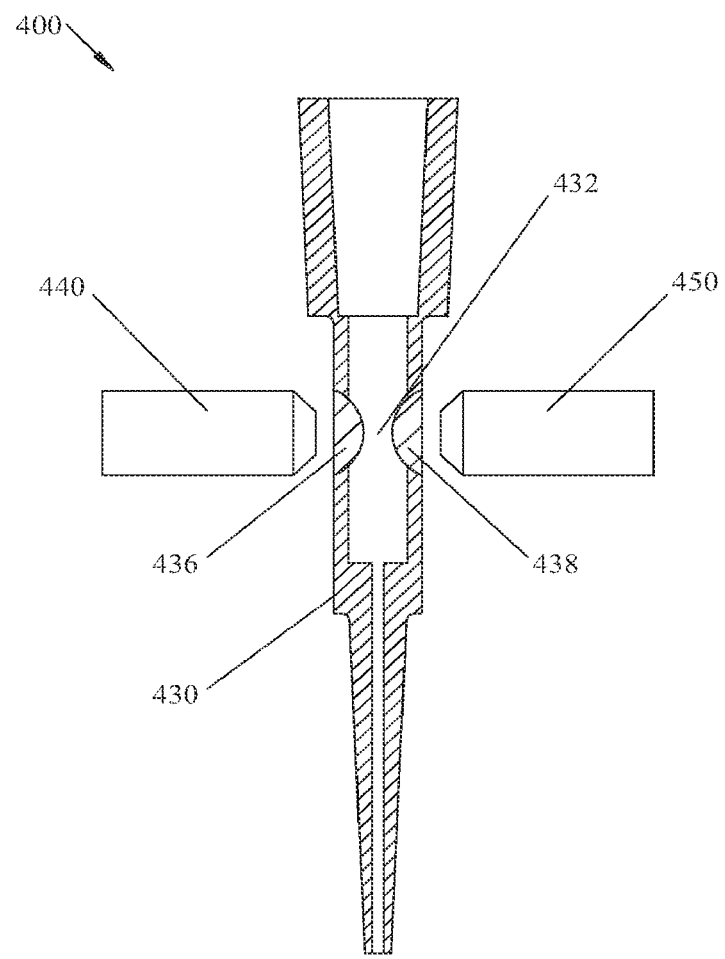
FIG. 4 illustrates an elevational view of exemplary embodiment of the system.

Now referring to FIG. 4 a third exemplary embodiment 400 for an exemplary pipette tip 430 according to this disclosure is illustrated. As shown in FIG. 4, the exemplary pipette tip 430 can be formed to include one or more optics components 436,438 (not necessarily to scale) in at least one observation zone 432 between the light supplying unit 440 and the light collecting unit 450, the optics component(s) 436,438 being usable to specify a focal/path length, and focal/path characteristics as the light traverses the liquid sample under observation, measurement and analysis.

In these embodiments, one or both of the light supplying unit and the light collecting unit can include certain optics adjustment components, including, but not limited to, one or more lenses, mirrors, windows, and/or filters between the light supplying unit and the pipette tip and/or between the pipette tip and the light collecting unit.

Those of skill in the art will recognize that varying physical and focal lengths for the light-transmissive paths through the liquid sample can improve an accuracy of the illumination/absorption measurements for the liquid sample.

Figure 5:
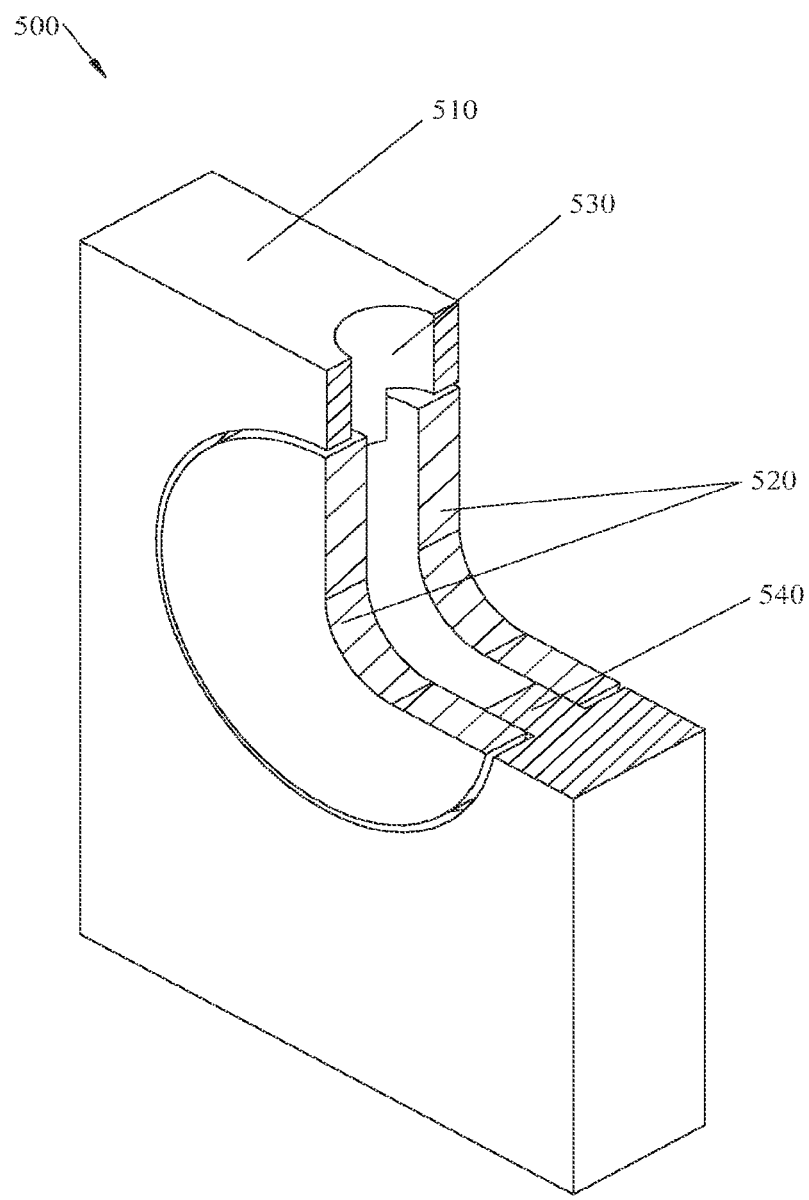
FIG. 5 illustrates an isometric view of a cartridge.

Example 1 Measurement of Light Intensity Through Quartz with a Known Path Length Utilizing Self-Location Methods Now referring to FIG. 5 a cartridge 500 made of a machined piece 510, and two quartz discs 520 assembled to be water tight with an opening to deposit liquids through a hole 530 in the top of the machined piece 510 is illustrated. The machined piece 510 had a lip 540 with known thickness to which one quartz disc 520 was adhered to each side. This configuration created a known path length between the two inside surfaces of the quartz discs.

Figure 6:
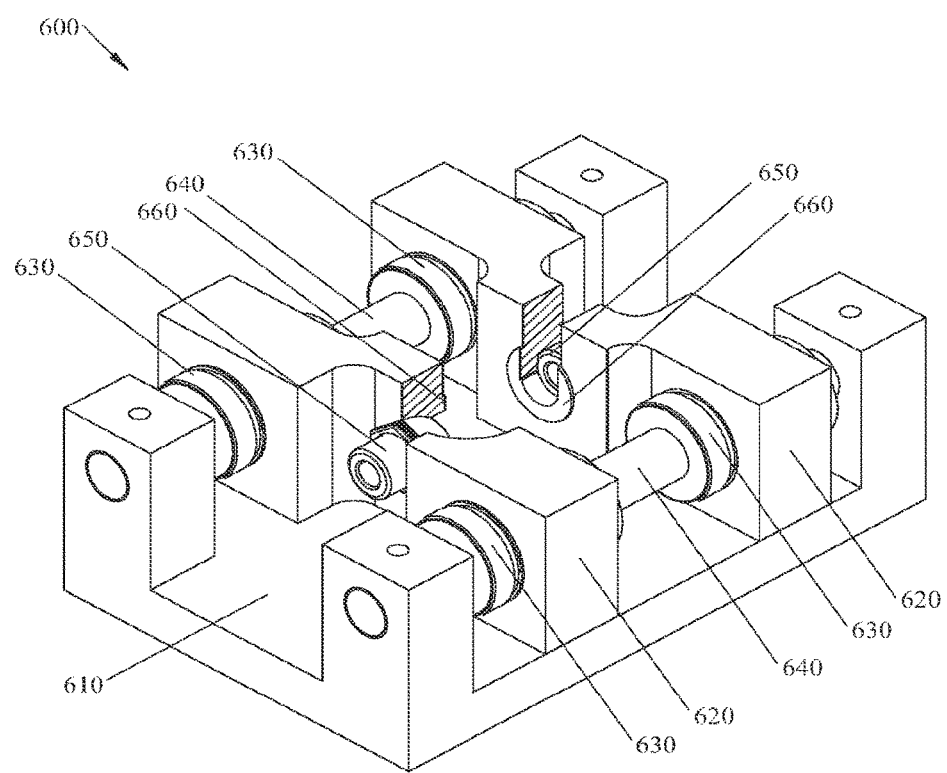
FIG. 6 illustrates an isometric view of a base.

Now referring to FIG. 6 a base 600 made of a machined base plate 610, two machined bearing blocks 620, linear bearings 630, two precision shafts 640, and two threaded fiber bushings 650 is illustrated. The bearing blocks 620 had a lip 660 on one side, and a threaded hole through the center in order to attach the threaded fiber bushings 650.

Figure 7:
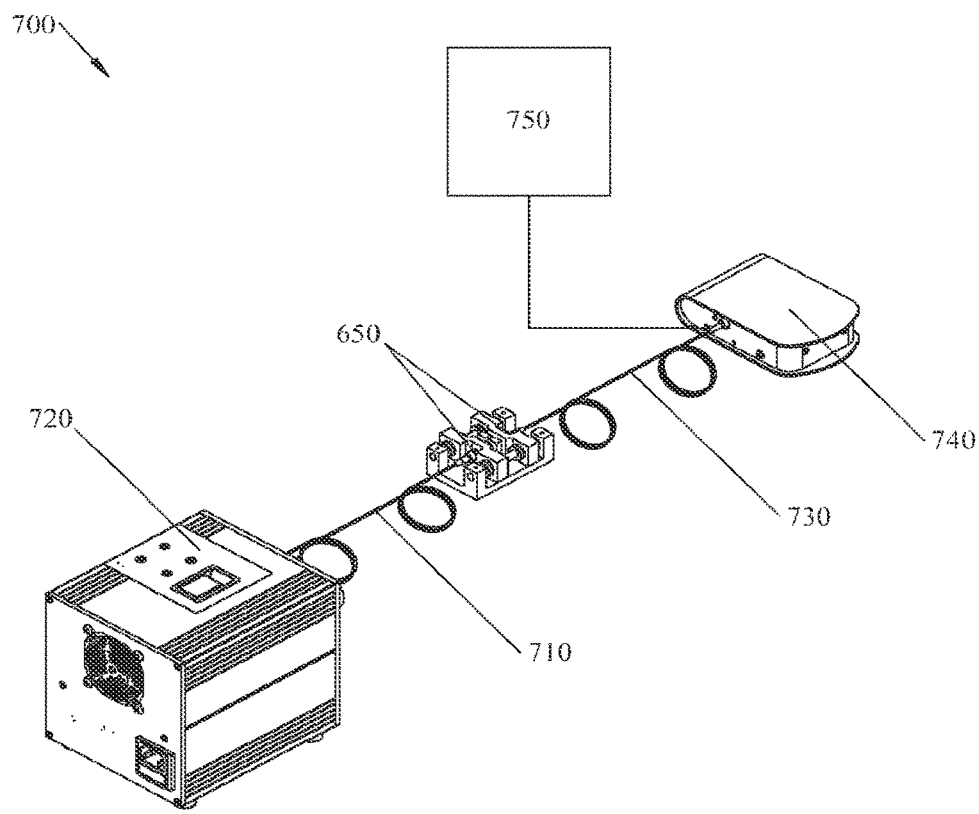
FIG. 7 illustrates an exploded isometric view of a system.

Now referring to FIG. 7 a system 700 that was created by connecting a fiber optics cable with quartz core 710 to a light source 720 on one end, and to one of the threaded fiber bushings 650 on the other end is illustrated. A second fiber optics cable 730 having a quartz core larger than 710 was connected to the remaining threaded fiber bushing 650 on one end, and to a spectrometer 740 on the other end. The spectrometer 740 fed into a personal computer 750 with software appropriate for graphical interpretation of the spectrometer's 740 signal in order to measure light intensity.

The cartridge 500 was placed approximately in the center between the two bearing blocks 620 with minimal support by a loose fitting slot machined into base plate 610. The bearing blocks 620 were moved along the linear bearings 630 to allow the lips 660 to come into contact with the quartz discs 520. This interaction aligned the fiber optics cables 710 and 730 perpendicular with the quartz discs 520. Measurements of light intensity were taken from this configuration.

Measurements were taken with air between the quartz discs 520 in cartridge 500, and water for comparison. Between every measurement the cartridge 500 was removed from the base 600, and replaced in order to create non-repeating starting locations of the cartridge 500 for each measurement. The results of these measurements can be seen in TABLE 1.

TABLE 1

| Air at 701.2936 nm | | Water at 701.2936 nm | |
| --- | --- | --- | --- |
| Measurement | Intensity | Measurement | Intensity |
| 1 | 0.71867 | 1 | 0.89449 |
| 2 | 0.72413 | 2 | 0.89707 |
| 3 | 0.72577 | 3 | 0.90385 |
| 4 | 0.73195 | 4 | 0.90395 |
| 5 | 0.73655 | 5 | 0.91473 |
| STDEV | 0.006964 | STDEV | 0.007852 |
| Max | 0.73655 | Max | 0.91473 |
| Min | 0.71867 | Min | 0.89449 |
| Range | 0.01788 | Range | 0.02024 |

The results in TABLE 1 correspond to respective linear regression lines with R-squared values greater than 0.9 each. A person familiar with this value will recognize there is a clear linear trend. Using personal computer 750 intensity values integrated over time would yield precise intensity measurements, which in turn produce precise absorbance/fluorescence measurements.

Example 1 is analogous to inserting a pipette tip into a mechanism, and relying on the mechanism to create the necessary perpendicularity.

Specific reference to, for example, the above-discussed embodiments for the disclosed pipette tip, and the characteristics thereof, should not be interpreted to constrain the disclosed pipette tip to only those embodiments. The depicted and described embodiments are included for non-limiting illustration of the disclosed products for implementing systems, methods, techniques, processes and schemes for liquid sample observation, measurement and analysis, which should, therefore, be interpreted and as being exemplary only, and not limiting the disclosed schemes, in any manner.

Features and advantages of the disclosed embodiments are set forth in this disclosure and can be, at least in part, obvious from this detailed description, or can be learned by practice of the disclosed embodiments. The features and advantages of the disclosed embodiments can be realized and obtained by means of the instruments and combinations of features particularly described.

Various embodiments of the disclosed systems and methods are discussed in this disclosure. While specific implementations are discussed, it should be understood that this is done for illustration purposes only. A person skilled in the relevant art will recognize that other components and configurations can be used without departing from the spirit and scope of the disclosed embodiments.

The invention claimed is:

1. A measuring system comprising:
a self-alignment device comprised of a base unit configured to receive a pipette tip, said base unit configured to provide structural alignment of the pipette tip between a light source and a light collector mounted to the base unit, wherein said base unit has an inner profile defining an accommodating space, wherein said inner profile of the base unit is configured to physically interact with an outer profile of a holder configured to secure the pipette tip during measurement and
the pipette tip containing a liquid sample; wherein the light emitted by the light source passes through the pipette tip containing the liquid sample, and the light is collected by the light collector, wherein said pipette tip is configured to have at least one optically clear set of parallel flats, said at least one optically clear set of parallel flats defining one or more cross-sectional path lengths through the liquid sample.

2. The self-alignment device of claim 1 further comprising one or more optics components positioned between the light source and the light collector.

3. The self-alignment device of claim 1 further comprising: at least one optics component positioned between the light source and the light collector to define a focal path length.

4. A method to position a discrete pipette tip in a light measuring system to measure light transmission comprising: providing a self-alignment structure made of a base unit configured to receive a pipette tip, said base unit configured to provide structural alignment of the pipette tip between at least one light source and at least one light collector mounted to the base unit, wherein said base unit has an inner profile defining an accommodating space, wherein said inner profile of the base unit is configured to physically interact with an outer profile of a holder configured to secure the pipette tip;
wherein said pipette tip is configured to have at least one optically clear set of parallel flats, said at least one optically clear set of parallel flats defining one or more cross-sectional path lengths through the liquid sample, inserting the pipette tip into said self-alignment structure; adding a liquid sample to the pipette tip;
positioning the pipette tip through interaction with the base unit, wherein the pipette tip is positioned between the light source and light collector to allow light to pass through the pipette tip and measuring light transmission through the liquid sample while the pipette tip contacts the self-alignment structure.

5. The method of claim 4 further comprising the step of recovering the pipette tip with the liquid sample inside of said pipette tip.

6. The method of claim 5 further comprising the step of sealing the tip with the liquid.

7. The method of claim 4 further comprising the step of aligning said at least one optically clear set of parallel flats of said pipette tip with the at least one light source.

8. The method of claim 4 further comprising the steps of aligning said at least one optically clear set of parallel flats of said pipette tip with at least one light collector.

9. The method of claim 4 wherein said at least one optically clear set of parallel flats is comprised of quartz.

10. The method of claim 4 wherein said pipette tip is configured to comprise at least one optics component, further comprising the steps of aligning said at least one optics component of said pipette tip with at least one light source.

11. The method of claim 4 wherein said pipette tip is configured to comprise at least one optics component, further comprising the steps of aligning said at least one optics component of said pipette tip with at least one light collector.

12. The method of claim 4 wherein said pipette tip is configured to comprise at least one optics component including a reflective coating, further comprising the steps of aligning said at least one optics component of said pipette tip with at least one light source.

13. The method of claim 4 wherein said pipette tip is configured to comprise at least one optics component including a reflective coating, further comprising the steps of aligning said at least one optics component of said pipette tip with at least one light collector.

14. The method of claim 13 further comprising the step of analyzing the liquid sample.

* * * * *